(12) United States Patent
Kawata et al.

(10) Patent No.: US 6,370,485 B1
(45) Date of Patent: Apr. 9, 2002

(54) SIGNAL PROCESSING APPARATUS AND NON-DESTRUCTIVE TESTING APPARATUS USING THE SAME

(75) Inventors: Kayoko Kawata, Hyogo-ken; Shintaro Kumano, Tokyo; Mitsuyoshi Matsumoto, Hyogo-ken, all of (JP)

(73) Assignee: Mitsubishi Heavy Industries, Ltd., Tokyo (JP)

( * ) Notice: Subject to any disclaimer, the term of this patent is extended or adjusted under 35 U.S.C. 154(b) by 0 days.

(21) Appl. No.: 09/366,202

(22) Filed: Aug. 4, 1999

(30) Foreign Application Priority Data

Aug. 5, 1998 (JP) .......................................... 10-233627

(51) Int. Cl.[7] .............................................. G01L 23/06
(52) U.S. Cl. ...................................... 702/113; 702/182
(58) Field of Search ................................ 702/113, 182, 702/184, 185, 180, 188, 189, 191, 57, 66, 67, 69, 70, 71, 74, 75, 76, 77, 106, 108, 122, 124, 126, 179, 193, 195, 196, 197

(56) References Cited

U.S. PATENT DOCUMENTS

| 5,224,174 A | * | 6/1993 | Schneider et al. | .............. 382/5 |
| 5,299,577 A | * | 4/1994 | Brown et al. | .......... 128/660.07 |
| 5,431,693 A | * | 7/1995 | Schroeppel | .................. 607/28 |
| 5,671,155 A | | 9/1997 | Edens et al. | ................. 364/507 |
| 5,864,773 A | * | 1/1999 | Barna et al. | ................... 702/85 |
| 6,263,355 B1 | * | 7/2001 | Harrell et al. | ............... 708/320 |

FOREIGN PATENT DOCUMENTS

CA          2275577          7/1998

* cited by examiner

*Primary Examiner*—Marc S. Hoff
*Assistant Examiner*—Edward Raymond
(74) *Attorney, Agent, or Firm*—Sughrue Mion, PLLC

(57) ABSTRACT

A signal processing apparatus includes a 2-dimensional conversion processing section, a 2-dimensional emphasis and attenuation processing section and a 2-dimensional smoothing processing section. The 2-dimensional conversion processing section maps an observation signal in a first coordinate system onto a second coordinate system to output a 2-dimensional converted signal. The observation signal includes a detection object component and a noise component to be attenuated. The noise component is composed of a first noise component and a second noise component. The 2-dimensional emphasis and attenuation processing section attenuates the first noise component to emphasize the detection object component and outputs a 2-dimensional filtered signal in which the detection object component is emphasized. The 2-dimensional smoothing processing section attenuates the second noise component contained in the 2-dimensional filtered signal, and outputs a 2-dimensional smoothing signal, whereby a detection object can be detected based on the 2-dimensional smoothed signal.

20 Claims, 14 Drawing Sheets

ORIGINAL SIGNAL           DIFFERENTIAL RESULT

|   | −1 |   |
|---|----|---|
| −1 | 4 | −1 |
|   | −1 |   |

SIGNAL PROCESSING APPARATUS AND NON-DESTRUCTIVE TESTING APPARATUS USING THE SAME

BACKGROUND OF THE INVENTION

1. Field of the Invention

The present invention relates to a signal processing apparatus and a non-destructive testing apparatus using the same. More particularly, the present invention relates to a signal processing apparatus and a non-destructive testing apparatus using the same, in which the difference between a signal component and a noise component in spatial frequency component is used for noise reduction.

2. Description of the Related Art

Pipes with various diameters are used in a large-scaled plants such as atomic generation plants and thermal power generation plants. These pipes are subject to influences such as vibration and heat change. As a result of these influences, flaws or damage sometimes occurs inside the pipe. In order to ensure the safety of the operation of the large-scaled plant, the pipes need to be tested to see if any flaw or damage has occurred. A non-destructive test is usually performed.

There are various conventional non-destructive test methods. Known general non-destructive test methods include a supersonic flaw detecting method and an eddy current testing method.

In the eddy current test (ECT) method, small flaws can be detected, however, the results can be influenced by noise. A sensor used in the eddy current test is generally a rotary type sensor, which is rotated in a circumferential direction in a test body, such as a pipe, while progressing in an axial direction into the test body. Eddy current is generated in a metal body of the test body by a moving magnetic field generating body or a stationary magnetic force changing coil. The magnetic force generated by the eddy current is measured as a function of a position coordinate.

A noise component comprises a support structure noise component, a pipe diameter change noise component, an adhesion noise component, a sensor fluctuation noise component and an electric noise component. Techniques such as (1) a band pass filtering method, (2) a multiple frequency calculating method and (3) a line filtering method are conventional methods that are used to remove these noise components.

In the band pass filtering method, a signal is observed from the test body, such as a pipe, as a time series signal, and a component of the signal, other than a specific frequency band, is attenuated. This band pass filtering method will be described with reference to FIG. 1. First, in order to analyze in a frequency region, a observation signal x(n), as the time series signal, is converted (Fourier transform) from a time space into a frequency space so that a frequency spectrum X(f) is obtained. The observations signal X(n) comprises a noise component and a damage component, as a detection object component, which indicates the existence and shape of any damage in the test body.

Next, a weighting operation is performed on the frequency spectrum X(f) by using a band pass window having the frequency response of w(f) to obtain a frequency spectrum X'(f). The weighting operation attenuates the frequency component, other than the specific frequency region. In order to obtain a band pass signal X'(n) after the filtering, an inverse Fourier transform is performed to the band pass signal X'(f) to obtain a band pass signal X'(n) as a time series signal in which the frequency component, other than the specific frequency band, is attenuated.

FIG. 2 shows the multiple frequency calculating method. In this method, the way of changing a detected signal is different, depending on a signal generation factor, when an excitation frequency is different. In the multiple frequency calculating method, a linear calculation of a multiple frequency signal (X1 (t), X2(t), X3(t) and X4(t)) is performed by using filtering parameters (W1, W2, W3 and W4) previously set to output a synthetic signal Y(t) in which only a damage component as a detection object component remains.

FIGS. 3A and 3B show the line filtering method. In this method, a component for one line specified as a reference line is removed from a 2-dimensionally distributed original signal.

In the above-mentioned band pass filtering method, the frequency spectrum of the observed time series signal is analyzed by paying attention to 1-dimensional component of the 2-dimensionally distributed signal. Therefore, the detected frequency response is easy to change depending upon the directions of the detection object component and noise component.

Another problem is that the signal obtained after the filtering operation looks like vibration. Therefore, the position precision is degraded when attempting to narrow the band width of the filter.

The multiple frequency calculating method is effective when the phase angles of the of the detection object component and noise component are clearly different. However, when the phase angles are close to each other, the filtering effect is low. For example, phase angles are close to each other when there is a damage signal and a deformation signal on the surface of the test body on side of the sensor.

Moreover, the line filtering method reduces a uniformly distributed noise component in a 1-dimensional direction of the 2-dimension. However, the reduction is minimized when there is a noise component other than the uniformly distributed noise component in the 1-dimensional direction. Also, even if the noise component is uniformly distributed in the 1-dimensional direction, an unnecessary component remains when the uniformity is not broken due to the drift and so on. Moreover, the reference line as the main point of the line filtering method should be estimated based on the observation signal. Therefore, there is a risk that the detection object component will be attenuated when a mistake is present in the estimation.

In the eddy current testing method, the properties of the damage such as direction, length, width and depth have various values. However, because a detection signal is obtained by observing the change of the eddy current flowing through the test body, the frequency components of the detection signal are spread 2-dimensionally in accordance with the excitation frequency, even if the damage is small.

On the other hand, the noise component is different from the damage component as a detection object component in a 2-dimensional spatial frequency spectrum. The noise component comprises the pipe support structure noise component, the pipe diameter change noise component, the adhesion noise component and the sensor fluctuation noise component. The noise component has a low frequency component in at least one of the 2 dimensions, as compared with the spatial frequency spectrum of the damage component. On the other hand, the electric noise component has a frequency component higher than the spatial frequency spectrum of the damage component.

SUMMARY OF THE INVENTION

An object of the present invention is to provide a signal processing apparatus which has a highly precise detection ability, and in which the filtering technique is used based on the difference between a detection object component and a noise component to be attenuated in a spatial frequency spectrum.

Another object of the present invention is to provide a non-destructive testing apparatus using the above signal processing apparatus.

In order to achieve an aspect of the present invention, a signal processing apparatus includes a 2-dimensional interpolation processing section, a 2-dimensional emphasis and attenuation processing section and a 2-dimensional smoothing processing section. The 2-dimensional interpolation processing section maps an observation signal in a first coordinate system into a second coordinate system to output a 2-dimensional interpolation signal. The observation signal includes a detection object component and a noise component to be attenuated, and the noise component is composed of a first noise component and a second noise component. The 2-dimensional emphasis and attenuation processing section attenuates the first noise component to emphasize the detection object component and outputs a 2-dimensional filtering signal in which the detection object component is emphasized. The 2-dimensional smoothing processing section attenuates the second noise component contained in the 2-dimensional filtering signal, and outputs a 2-dimensional smoothing signal, whereby a detection object can be detected based on the 2-dimensional smoothing signal.

The 2-dimensional emphasis and attenuation processing section may include a 2-dimensional digital differential filter. Also, the 2-dimensional smoothing processing section may include a median filter.

In order to achieve another aspect of the present invention, a non-destructive testing apparatus includes a detector, a display unit and a processor. The detector measures a test object and generates a measurement signal in a first coordinate system. The processor maps the measurement signal in the first coordinate system onto a second coordinate system to produce a second coordinate system measurement signal, removes a noise component from the second coordinate system measurement signal to produce a resultant signal, and controls the display unit to display the resultant signal.

The detector may be a rotary type detector, wherein the first coordinate system is a polar coordinate system, or a multi-coil type sensor, wherein the first coordinate system is a 2-dimensional coordinate system.

Also, the second coordinate system may be a 2-dimensional orthogonal coordinate system. In this case, the processor converts each of the values of the measurement signal to a value on the 2-dimensional orthogonal coordinate system, while mapping the measurement signal in the first coordinate system onto the 2-dimensional orthogonal coordinate system.

Also, the processor may attenuate a part of the noise component from the second coordinate system measurement signal. In this case, the processor may attenuate the part of the noise component from the second coordinate system measurement signal using a first frequency cutting type filter. In addition, the filter may be a 2-dimensional digital differential filter.

Also, the processor may remove the remaining part of the noise component from the second coordinate system measurement signal. In this case, the processor smoothes the second coordinate system measuring signal to remove the remaining part of the noise component from the second coordinate system measurement signal. Moreover, the processor smoothes the second coordinate system measuring signal using a filter to remove the remaining part of the noise component from the second coordinate system measurement signal. The filter may be a median filter.

In order to achieve still another aspect of the present invention, a non-destructive testing method of a test object includes:

measuring a test object to generate a measurement signal in a first coordinate system;

mapping the measurement signal in the first coordinate system onto a second coordinate system to produce a second coordinate system measurement signal;

removing a noise component from the second coordinate system measurement signal to produce a resultant signal; and providing information of the test object based on the resultant signal.

In order to achieve yet still another aspect of the present invention, a non-destructive testing apparatus includes:

a detector measuring a test object to generate a measurement signal in a first coordinate system;

a display unit;

a first filter that attenuates a first frequency region of an input signal to produce a first filtered resultant signal;

a second filter that attenuates a second frequency region of an input signal to produce a second filtered resultant signal, the second frequency region being apart from the first frequency region; and a processor that:
maps the measurement signal in the first coordinate system onto a second coordinate system adaptable for the first filter,
selectively maps a first filtered resultant signal in the second coordinate system into a third coordinate system adaptable for the second filter, and
controls the display unit to display a second filtered resultant signal.

DESCRIPTION OF THE PREFERRED EMBODIMENTS

A non-destructive testing apparatus that includes a signal processing apparatus of the present invention will be described in detail with reference to the attached drawings.

Figure 1:
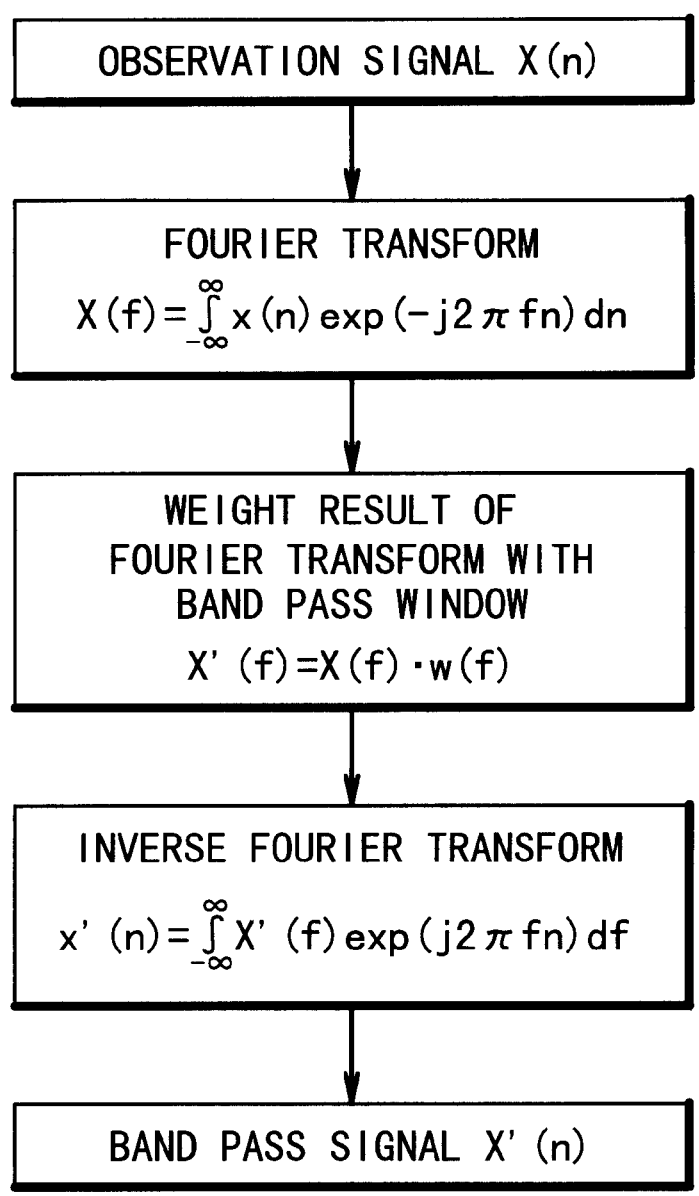
FIG. 1 is a diagram showing a conventional band pass filtering method.
Figure 2:
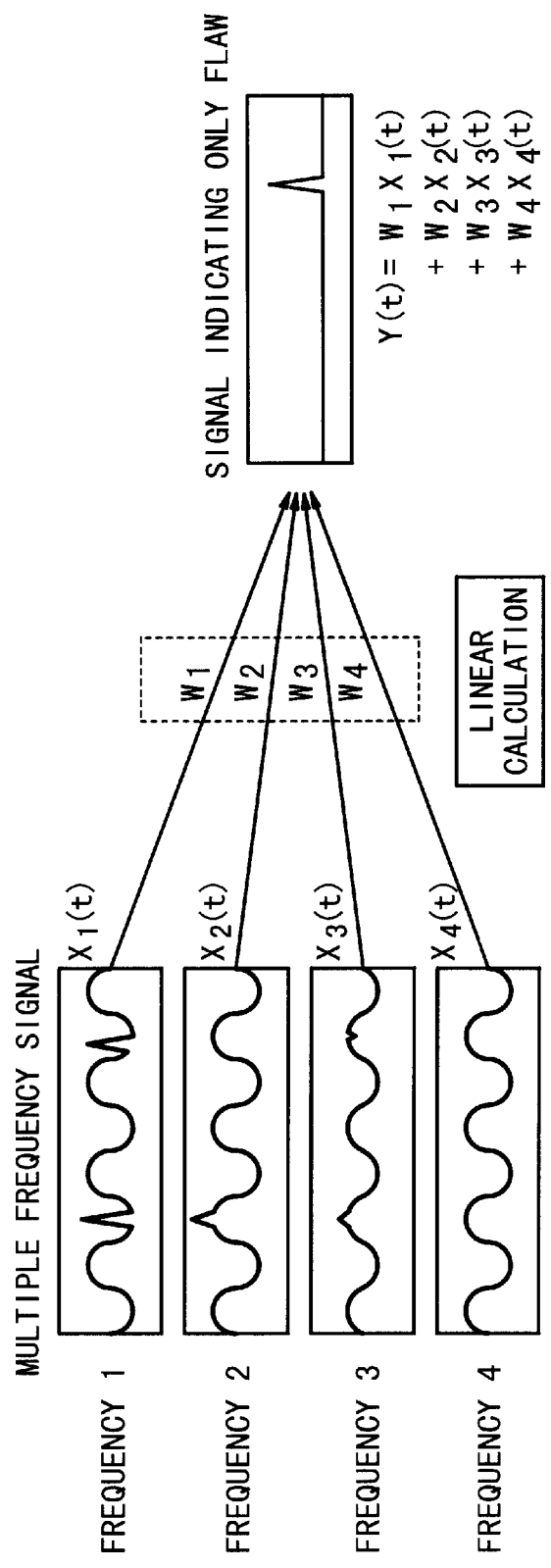
FIG. 2 is a diagram showing a conventional multiple frequency calculating method.
Figure 3:
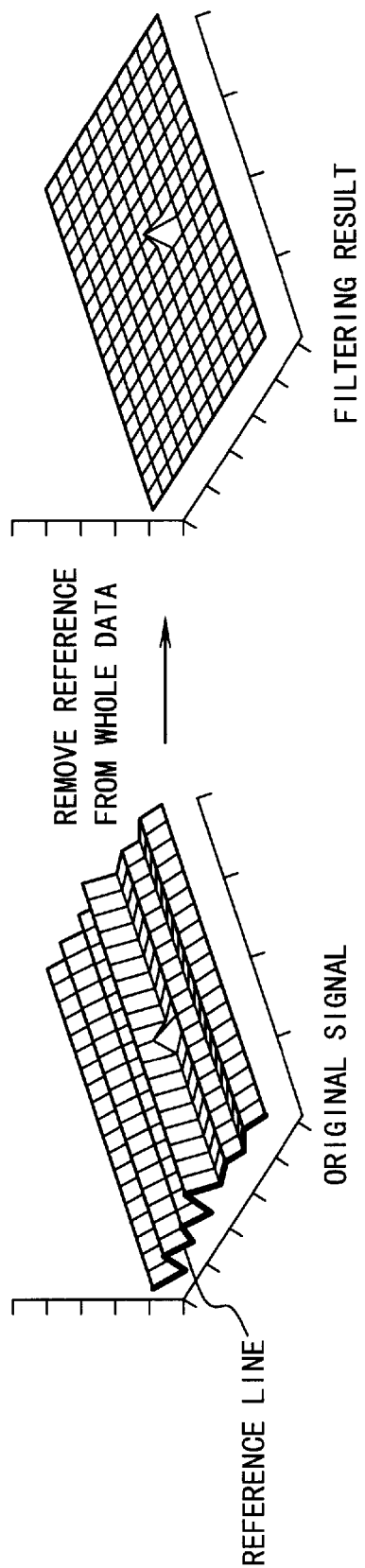
FIGS. 3A and 3B are diagrams showing a conventional line filtering method.
Figure 4:
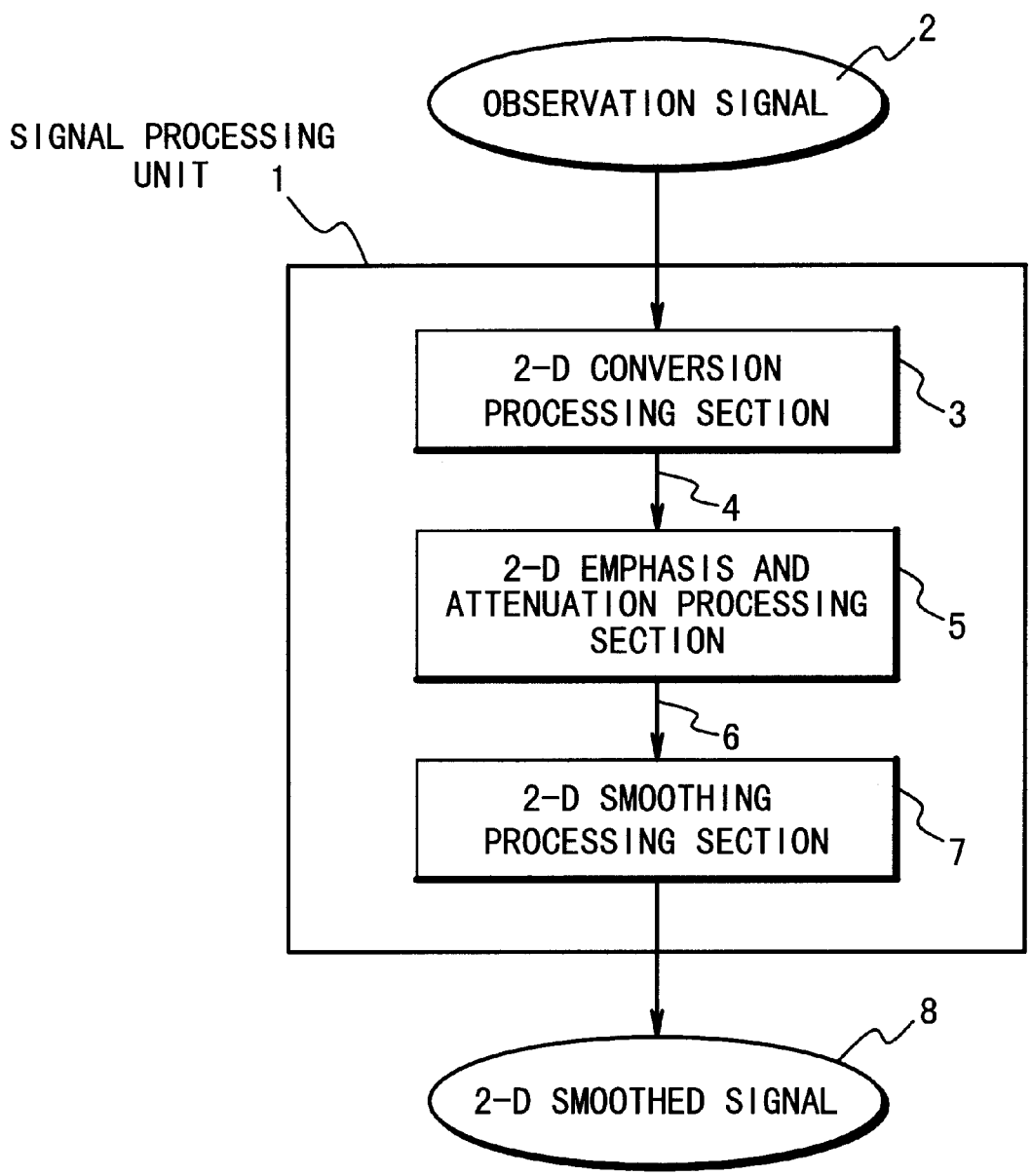
FIG. 4 is a block diagram illustrating a signal processing apparatus of a non-destructive testing apparatus according to an embodiment at of the present invention.

FIG. 4 shows the structure of the non-destructive testing apparatus that includes the signal processing unit according to an embodiment of the present invention. Referring to FIG. 4, the non-destructive testing apparatus includes a rotary type detector 2, a signal processing unit 1 and a display unit 8. The signal processing unit 1 may be a processor. The signal processor unit 1 includes a 2-dimensional conversion processing section 3, a 2-dimensional emphasis and attenuation processing section 5 and a 2-dimensional smoothing processing section 7.

Figure 5A:
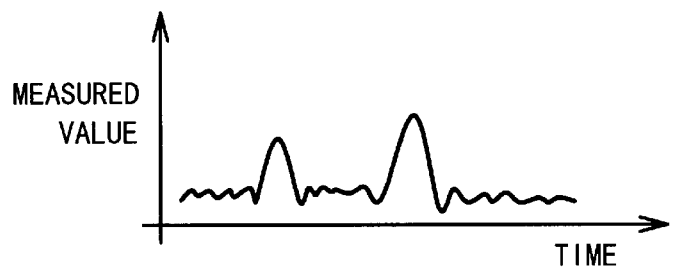
FIGS. 5A to 5C are diagrams showing a signal subjected to a mapping process in a rotary sensor.
Figure 5B:
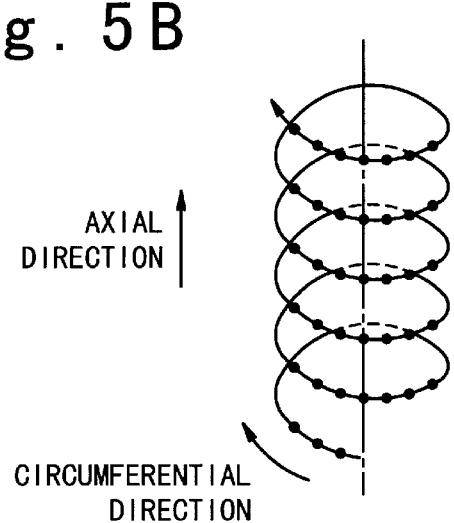
Figure 5C:
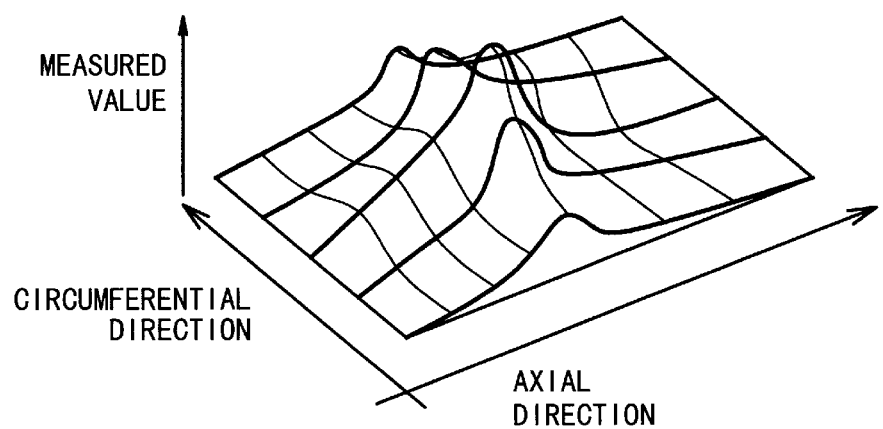
Figure 7B:
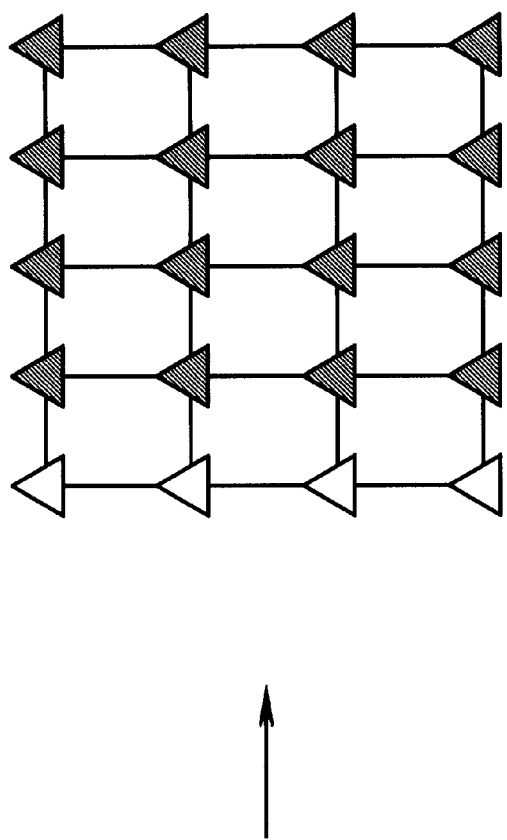
FIGS. 7A and 7B are diagrams showing the 2-dimensional mapping process.
Figure 7A:
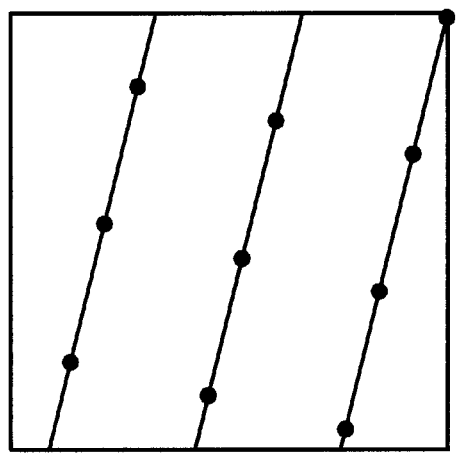

The 2-dimensional conversion processing section 3 is described below. Referring to FIGS. 5A to 5C, sample points of an observation signal detected by the detector 2 being used in an eddy current testing method are arranged in a spiral in correspondence with a test body, such as a pipe, as shown in FIG. 5B. The 2-dimensional conversion processing section 3 maps the observation signal from a polar coordinate system into the 2-dimensional orthogonal plane coordinate system. Thus, a 2-dimensional mapped signal is obtained, as shown in FIGS. 7A and 7B.

The damage component, as a detection object component, and a noise component are contained in the observation signal and the 2-dimensional mapped signal. The noise component is composed of an environment depending noise component and an electric noise component. The environment depending noise component is composed of a noise component based on a support structure of a pipe, a noise component based on the change of a pipe diameter, a noise component based on an adhesion and a noise component based on the fluctuation of a sensor.

Figure 8:
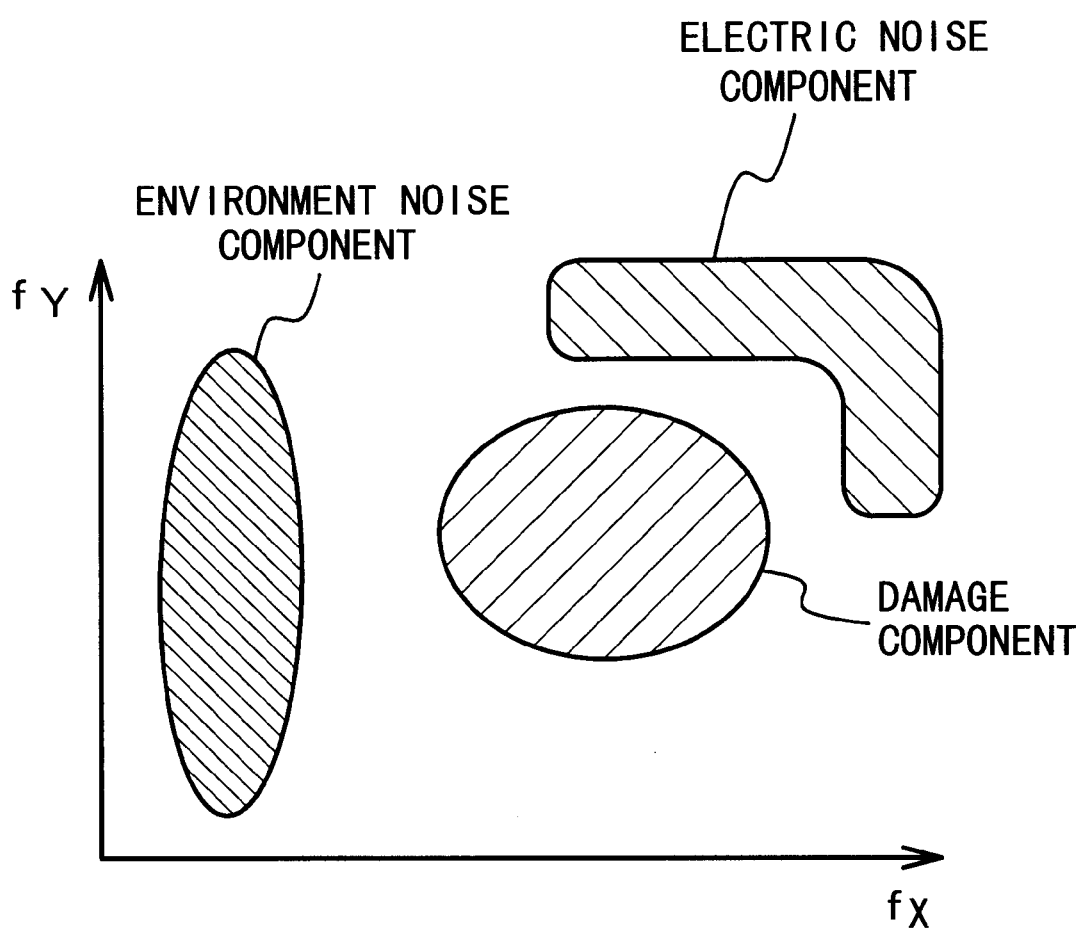
FIG. 8 is a diagram showing the position where each spectrum component in the spatial frequency region exists.

FIG. 8 shows the spectral component positions of the damage component, which include the detection object component, the environment noise component and the electric noise component, in the spatial frequency region. Frequencies fx fy are equivalent to the frequencies in the respective axes of the orthogonal plane coordinate system shown in FIG. 7B.

The environment noise component has the spectrum component in the low frequency region in at least one of the 2-dimensions, as compared with the spatial frequency spectrum component of the damage component. The electric noise component has the spectrum component in the frequency region higher than the spatial frequency spectrum component of the damage component. It should be noted that although the respective components are separated in the figure, the regions actually mutually overlap.

Based on the above, the 2-dimensional emphasis and attenuation processing section 5 attenuates the environment noise component contained in the 2-dimensional mapped signal to output a 2-dimensional filtered signal in which the damage component is emphasized. In this embodiment, a 2-dimensional digital differential filter is used in the 2-dimensional emphasis and attenuation section 5.

Next, the 2-dimensional smoothing processing section 7 attenuates the electric noise component as the high frequency component contained in the 2-dimensional filtered signal, to output a 2-dimensional smoothed signal. In this embodiment, a median filter is used in the 2-dimensional smoothing processing section 7.

Next, the operation processing of the signal processing unit 1 of the present invention will be described in detail.

Referring to FIGS. 5A to 5C and FIGS. 6A and 6B, the observation signal detected by the detector 2 in the eddy current testing method will be described first.

FIGS. 5A to 5C and FIGS. 6A and 6B show how the sample points are arranged 2-dimensionally in the eddy current testing method. FIG. 5A shows a sample signal detected by the rotary type detector 2. FIG. 5B shows an example of the sample points which are detected spirally in a constant interval in correspondence with the test body. In FIG. 5B, the sample points are indicated by black circles because the rotary type sensor is rotated while progressing into an axial direction of the test body.

If the observation signal is outputted as a function of time, a 1-dimensional time waveform is obtained, as shown in FIG. 5A. As shown in FIG. 5C, the axis direction of the test body, i.e., the direction of the movement of the rotary type detector 2, is set as a horizontal axis, and the circumferential direction is set as a vertical axis. In this case, the observation or measurement values can be obtained on a circular cylinder coordinate system or a spiral coordinate system. The points on the circular cylinder coordinate system or the polar coordinate system are converted or mapped onto points on an orthogonal plane coordinate system, and the intensities of the observation signal are shown in an axial direction which is orthogonal to the plane.

Figure 6A:
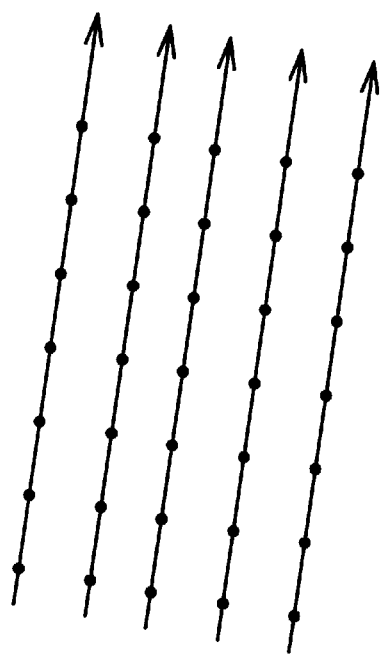
FIGS. 6A and 6B are diagrams illustrating the signal subjected to the mapping process in a multi-coil type detector.

Also, FIG. 6A shows the results obtained by a multi-coil type detector. This is a method of gathering samples in which a plurality of sensors fixed to each other in the position are moved in the same oblique direction, i.e., the direction not orthogonal to the direction of a row of the plurality of sensors.

Figure 6B:
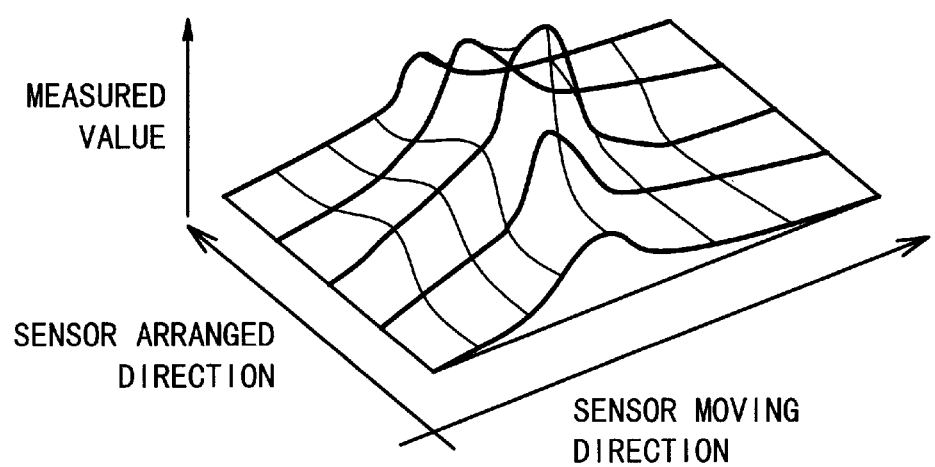

The black circles as sample points shown in FIG. 6A are not only arranged on a flat plane, but also on a circular cylinder plane. As shown in FIG. 6B, by setting the direction of the sensor movement to a horizontal axis and the direction of the sensor arrangement to a vertical axis, the observation values can be obtained.

The sample points obtained by the above-mentioned rotary type detector and the multi-coil type detector are not necessarily arranged in the axial direction of the test body. Therefore, it is necessary to map the detection signal in the spiral coordinate system or the polar coordinate system into the orthogonal plane coordinate system.

The 2-dimensional conversion processing section 2 converts the observation values of the observation signal shown in FIG. 7A from the rotary type detector or multi-coil type detector into observation values shown in FIG. 7B in the orthogonal plane coordinate system while interpolating or correcting the observation values. That is, the observation values are digitized for the orthogonal plane coordinate system. The interpolating or correcting process is executed during the digitizing process of the mapping process. The 2-dimensional conversion processing section 2 outputs the 2-dimensional mapped signal having interpolated processing values on the coordinate regions as shown in FIG. 7B. A symbol ▼ shows a sample point after the mapping process.

In this embodiment, the mapping process is carried out by using a linear interpolating process. Also, it become possible to apply a digital filtering technique, which is described later, by carrying out the interpolating process.

The 2-dimensional emphasis and attenuation processing section 5 calculates the damage component from the 2-dimensional mapped signal which is arranged in the orthogonal plane coordinate system. Then, the 2-dimensional emphasis and attenuation processing section 5 detects the damage component to output a 2-dimensional filtered signal. In this embodiment, the 2-dimensional digital differential filter is applied to the 2-dimensional emphasis and attenuation processing section 5.

The processing of the 2-dimensional digital differential filter is described below. In this embodiment, a differential type operator shown in FIG. 9B, and similar to the spatial differential operation, is used for the calculating the 2-dimensional mapped signal.

Figures 9A, 9B:
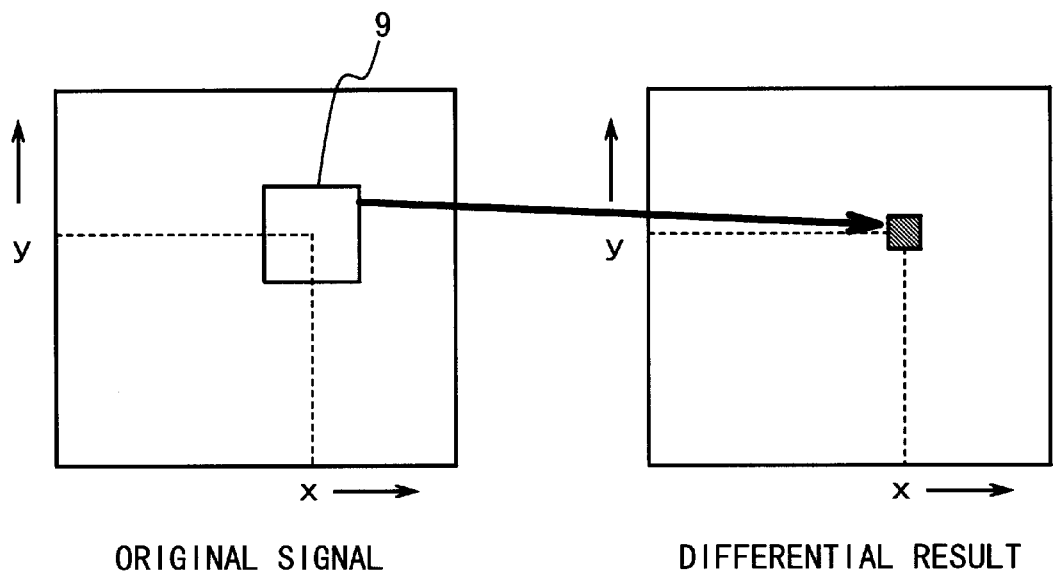
FIG. 9A is a diagram explaining the 2-dimensional digital differential filtering process.
FIG. 9B is a diagram showing an example of the differential type operator.

Referring to FIG. 9A, a convolution calculation is carried out on a signal contained in a local area 9 of the original signal arranged 2-dimensionally, i.e., the 2-dimensional mapped signal using the differential type operator or a differential pattern. It should be noted that the differential type operator shown in FIG. 9B is used in this embodiment. The differential type operator must be selected depending upon the size of the local area 9 and the direction.

In the convolution calculation processing using the differential type operator shown in FIG. 9B, a signal component which is uniformly distributed over the X- and Y-axes in FIG. 9A is able to be attenuated. That is, the signal component in the axial direction and the circumferential direction of the test body can be attenuated. In this way, the environment noise component contained in 2-dimensional mapped signal can be attenuated. The environment noise component exists in a low frequency region in at least one of the x-axis and the Y axis.

The 2-dimensional smoothing processing section 7 carries out the smoothing process to the 2-dimensional filtered signal and outputs a 2-dimensional smoothed signal. In this embodiment, a median filter is applied to the 2-dimensional smoothing processing section 7.

The median filter outputs a signal value contained in the local area 9 as a signal value in a corresponding local area in the orthogonal plane coordinate system in which a 2-dimensional filtered signal is accommodated.

Through this calculation processing, the intensity (concentration) change becomes gradual between the respective local areas in the signals which are accommodated on the orthogonal plane coordinate system. This shows that the electric noise component of a high frequency component in the spatial frequency is attenuated.

Through the processing of the above signal processing unit 1, the noise component is attenuated in the observation signal and the damage component as a detection object component can be detected. The detected damage component is displayed on the display unit 8 by the signal processing unit 1.

It should be noted that the damage component never spreads over {(the width or length of the damage component before the processing)+(the width or length of the operator) }. Therefore, the degradation in the position precision is very low, unlike the conventional band pass filtering method.

The non-destructive testing apparatus with a signal processing unit of the present invention can detect the detection object signal with high precision. This is because the difference in the spatial frequency spectrum is considered between the damage component to be detected and the noise component to be attenuated, and the filtering technique is positively used. The comparison in the detection precision between the signal processing unit of the present invention and the conventional technology will be described below.

Figure 10A:
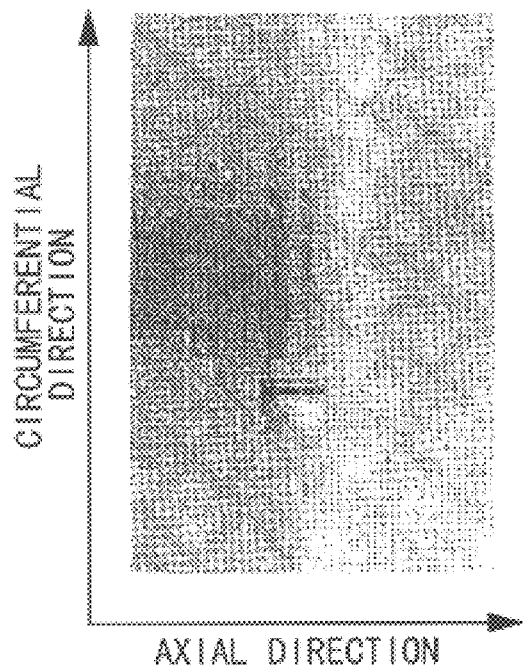
FIG. 10A is a color tone diagram explaining the result of mapping an observation signal onto a plane coordinate system.
Figure 10B:
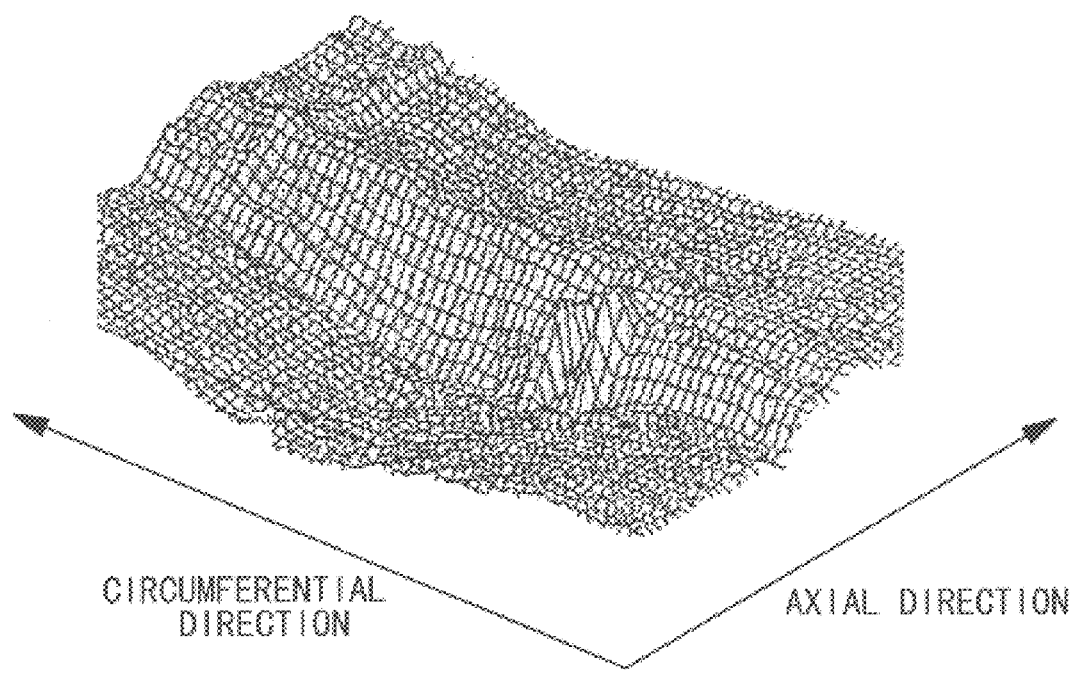
FIG. 10B shows a three-dimensional view of the result of the mapping.

FIGS. 10A and 10B are diagrams showing how an observation signal is mapped onto an orthogonal plane coordinate system by the 2-dimensional conversion processing section 3 of the present invention. FIG. 10a shows a color diagram, and FIG. 10B shows a three-dimensional eye view. In the color diagram, the horizontal axis represents an axial direction of the test body and the vertical axis represents a circumferential direction. Moreover, a signal value is represented by different shades of color. The signal value is larger as the color becomes brighter (the color is lighter).

Figure 11A:
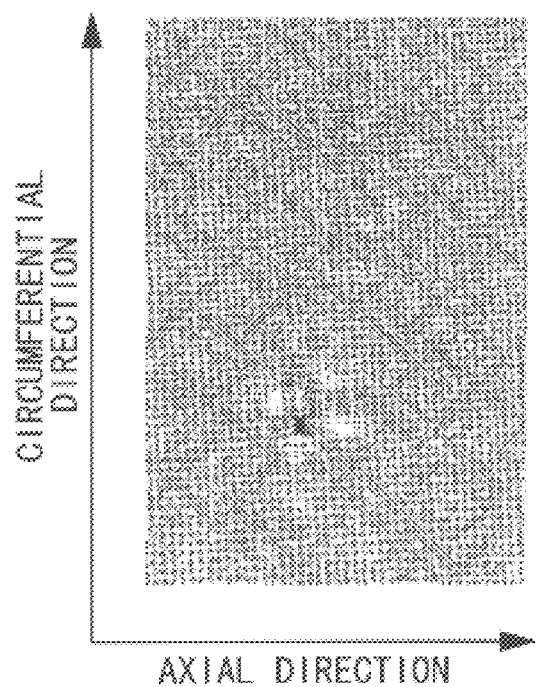
FIG. 11A is a color tone diagram showing a processing result by the signal processing apparatus of the present invention.
Figure 11B:
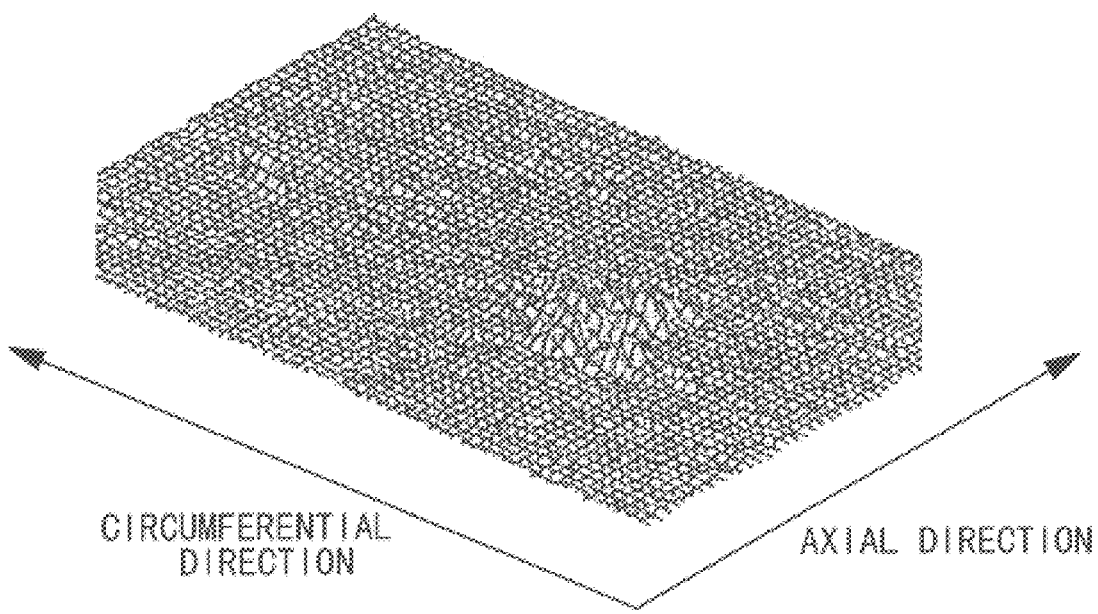
FIG. 11B shows a bird's eye view of the processing result.

FIGS. 11A and 11B are diagrams showing the processing result of the signal processing section of the present invention. FIG. 11A shows a color diagram, and FIG. 11B shows a three-dimensional view. It could be understood from these diagrams that the noise component is attenuated and only the damage component is detected clearly.

Figure 12A:
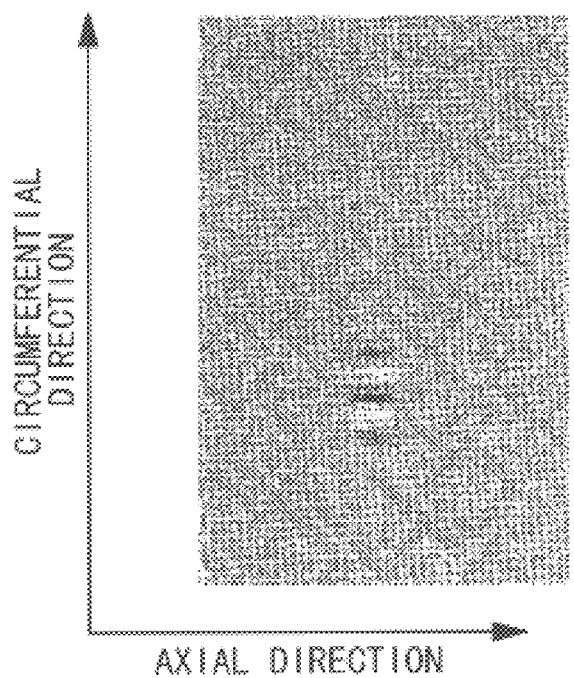
FIG. 12A is a color tone diagram showing a processing result by a conventional band pass filtering method.
Figure 12B:
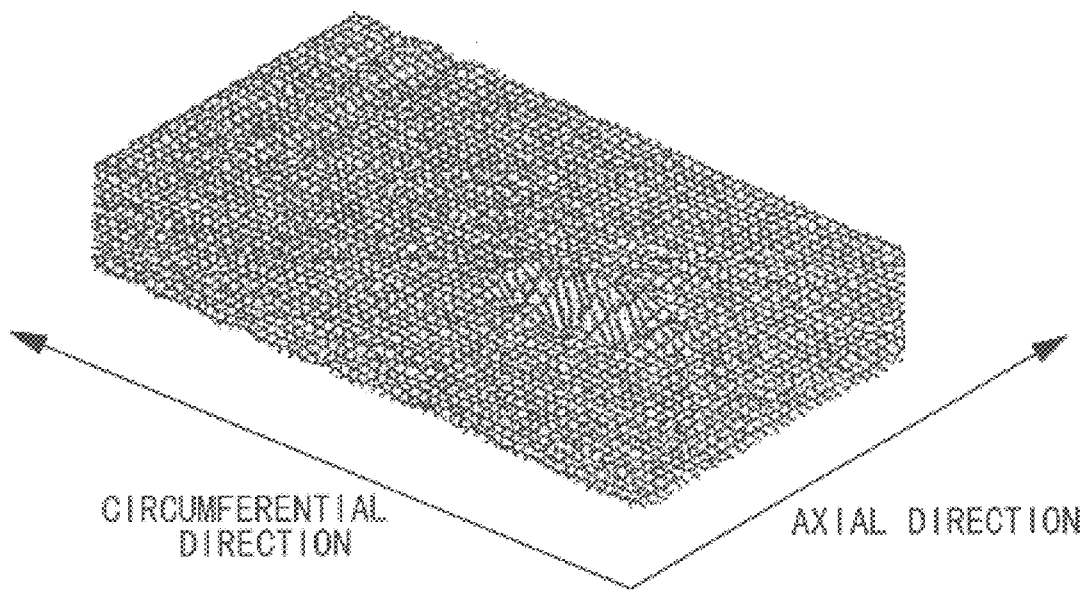
FIG. 12B shows a three-dimensional view of the processing result.

FIGS. 12A and 12B are diagrams showing a detection result by the conventional band pass filtering method. FIG. 12A shows a color diagram, and FIG. 12B shows a three-dimensional view.

Figure 13A:
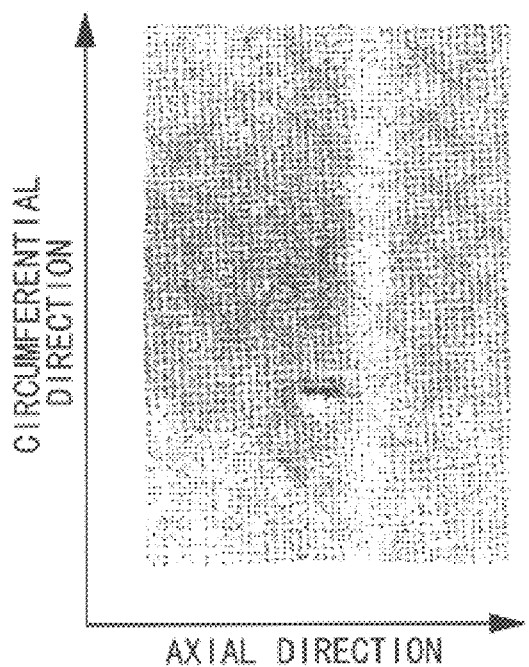
FIG. 13A is a color tone diagram showing a processing result by a conventional multiple frequency calculating method.
Figure 13B:
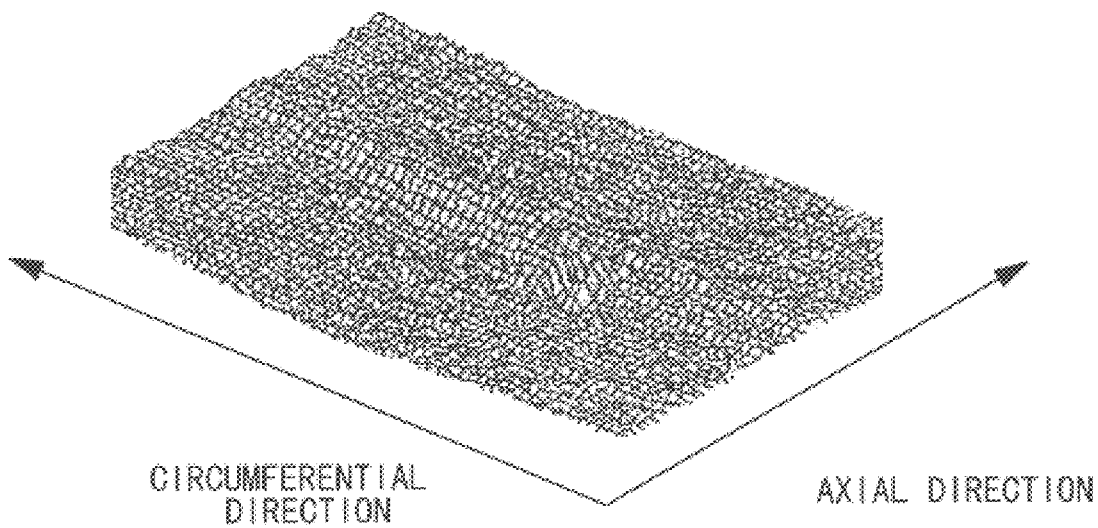
FIG. 13B shows a bird's eye view of the processing result.
Figure 14A:
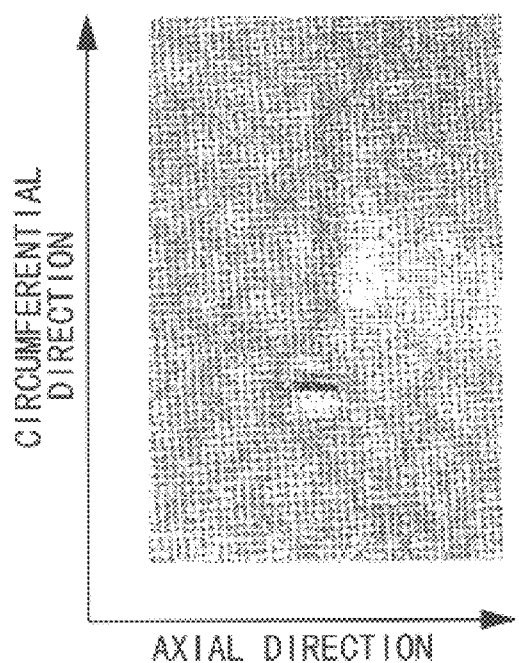
FIG. 14A is a color tone diagram showing a processing result by a conventional line filtering method.
Figure 14B:
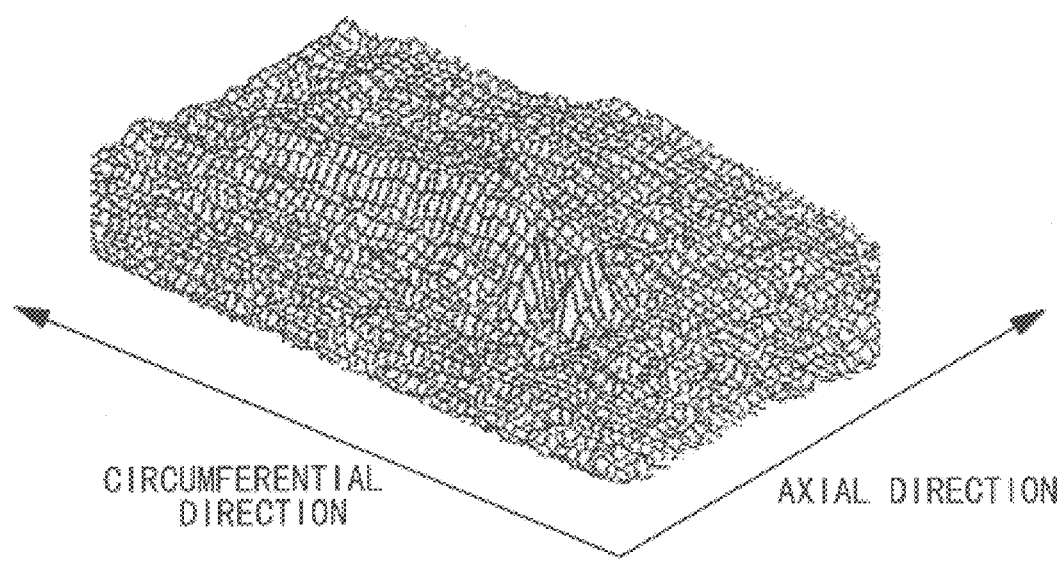
FIG. 14B shows a three-dimensional view of the processing result.

FIGS. 13A and 13B show a detection result by the conventional multiple frequency calculating method. FIG. 13A shows a color diagram, and FIG. 13B shows a three-dimensional view. FIGS. 14A and 14B show a detection result by the conventional line filtering. FIG. 14A shows a color diagram, and FIG. 14B shows a three-dimensional view.

It should be noted that in the color diagram, the horizontal axis represents an axial direction of the test body and the vertical axis represents a circumferential direction. Moreover, a signal value is represented by different shades of color. The signal value is larger as the color becomes brighter (the color is lighter).

In the detection results of the respective conventional techniques, the remainders of the noise component exist. Especially, in the band pass filter method, the damage component of the processing result spreads to the circumferential direction, and the position precision is decreased. From the above, the effectiveness of the signal processing section of the present invention is shown.

What is claimed is:

1. A signal processing apparatus comprising:
   a 2-dimensional conversion processing section which maps an observation signal in a first coordinate system into a second coordinate system to output a 2-dimensional converted signal, wherein said observation signal includes a detection object component and a noise component to be reduced, and said noise component is composed of a first noise component and a second noise component;

a 2-dimensional identification and reduction processing section which reduces said first noise component of said 2-dimensional converted signal to identify said detection object component thereof and outputs a 2-dimensional filtered signal in which said detection object component is identified from said noise component; and a 2-dimensional smoothing processing section which reduces said second noise component contained in said 2-dimensional filtered signal, and outputs a 2-dimensional smoothed signal, whereby a detection object can be detected based on said 2-dimensional smoothed signal.

2. A signal processing apparatus according to claim 1, wherein said 2-dimensional identification and reduction processing section includes a 2-dimensional digital differential filter.

3. A signal processing apparatus according to claim 1, wherein said 2-dimensional smoothing processing section includes a median filter.

4. A non-destructive testing apparatus comprising:
   a detector measuring a test object to generate a measurement signal in a first coordinate system;
   a display unit; and
   a processor:
      mapping said measurement signal in said first coordinate system onto a second coordinate system to produce a second coordinate system measurement signal,
      removing a noise component from said second coordinate system measurement signal to produce a resultant signal, and
      controlling said display unit to display said resultant signal.

5. A non-destructive testing apparatus according to claim 4, wherein said detector is a rotary type detector, and said first coordinate system is a polar coordinate system.

6. A non-destructive testing apparatus according to claim 4, wherein said detector is a multi-coil type sensor, and said first coordinate system is a 2-dimensional coordinate system.

7. A non-destructive testing apparatus according to claim 4, wherein said second coordinate system is a 2-dimensional orthogonal coordinate system, and
   wherein said processor approximately converts each of values of said measurement signal to a value on said 2-dimensional orthogonal coordinate system, while mapping said measurement signal in said first coordinate system onto said 2-dimensional orthogonal coordinate system.

8. A non-destructive testing apparatus according to claim 4, wherein said processor reduces a part of said noise component from said second coordinate system measurement signal.

9. A non-destructive testing apparatus according to claim 8, wherein said processor reduces the part of said noise component from said second coordinate system measurement signal using a filter of a first frequency cutting type.

10. A non-destructive testing apparatus according to claim 9, wherein said filter is a 2-dimensional digital differential filter.

11. A non-destructive testing apparatus according to claim 8, wherein said processor removes the remaining part of said noise component from said second coordinate system measurement signal.

12. A non-destructive testing apparatus according to claim 11, wherein said processor smoothes said second coordinate system measuring signal to remove the remaining part of said noise component from said second coordinate system measurement signal.

13. A non-destructive testing apparatus according to claim 12, wherein said processor smoothes said second coordinate system measuring signal using a filter to remove the remaining part of said noise component from said second coordinate system measurement signal.

14. A non-destructive testing apparatus according to claim 13, wherein said filter is a median filter.

15. A non-destructive testing method of a test object comprising:
   measuring a test object to generate a measurement signal in a first coordinate system;
   mapping said measurement signal in said first coordinate system onto a second coordinate system to produce a second coordinate system measurement signal;
   removing a noise component from said second coordinate system measurement signal to produce a resultant signal; and
   providing information of said test object based on said resultant signal.

16. A non-destructive testing method according to claim 15, wherein said second coordinate system is a 2-dimensional orthogonal coordinate system, and
   wherein said mapping includes approximately setting each of values of said measurement signal to a lattice value on said 2-dimensional orthogonal coordinate system, while mapping said measurement signal in said first coordinate system onto said 2-dimensional orthogonal coordinate system.

17. A non-destructive testing method according to claim 15, wherein said removing includes reducing a part of said noise component from said second coordinate system measurement signal.

18. A non-destructive testing method according to claim 15, said removing includes smoothing said second coordinate system measuring signal to remove the remaining part of said noise component from said second coordinate system measurement signal.

19. A non-destructive testing apparatus comprising:
   a detector measuring a test object to generate a measurement signal in a first coordinate system;
   a display unit; and
   a first filter filtering to reduce a first frequency region of an input signal to produce a first filtering resultant signal;
   a second filter filtering to reduce a second frequency region of an input signal to produce a second filtering resultant signal, said second frequency region being apart from said first frequency region; and
   a processor:
      executing mapping of said measurement signal in said first coordinate system onto a second coordinate system adaptable for said first filter,
      selectively executing mapping a first filtering resultant signal in said second coordinate system into a third coordinate system adaptable for said second filter, and
      controlling said display unit to display a second filtering resultant signal.

20. A non-destructive testing apparatus according to claim 19, wherein said processor controls said display unit to display a second filtering resultant signal without mapping said first filtering resultant signal in said second coordinate system into said third coordinate system, when the coordinate system is common to said first filter and said second filter.

* * * * *